United States Patent [19]

Slusarchyk et al.

[11] Patent Number: 4,551,276
[45] Date of Patent: Nov. 5, 1985

[54] 2-OXOAZETIDIN-1-YLOXYMETHYL SULFONIC ACID AND ANALOGS

[75] Inventors: William A. Slusarchyk, Belle Mead, N.J.; David Kronenthal, Yardley, Pa.

[73] Assignee: E. R. Squibb & Sons, Inc., Princeton, N.J.

[21] Appl. No.: 573,265

[22] Filed: Jan. 23, 1984

Related U.S. Application Data

[63] Continuation-in-part of Ser. No. 433,175, Oct. 6, 1982, abandoned.

[51] Int. Cl.$^4$ .................. C07D 205/08; C07D 403/12; C07D 401/12; A61K 31/395
[52] U.S. Cl. ............................ 260/239 A; 260/245.4; 260/239.3 R; 260/330.3; 260/330.9; 544/182; 544/215; 544/279; 544/327; 544/335; 544/336; 544/359; 546/189; 546/256; 546/208; 546/275; 514/210
[58] Field of Search ............ 260/239 A, 245.4, 330.3, 260/330.9, 239.3 R; 544/182, 215, 279, 327, 335, 336, 359; 546/189, 256, 208, 275

[56] References Cited

U.S. PATENT DOCUMENTS 4,337,197  6/1982  Gordon et al. ................. 260/239 A

FOREIGN PATENT DOCUMENTS 0051381  5/1982  European Pat. Off. .
2071650  9/1981  United Kingdom .

Primary Examiner—Mark L. Berch
Attorney, Agent, or Firm—Lawrence S. Levinson; Donald J. Barrack

[57] ABSTRACT

Antibiotic activity is exhibited by β-lactams having an

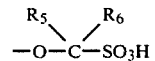

substituent in the 1-position and an acylamino substituent in the 3-position.

19 Claims, No Drawings

2-OXOAZETIDIN-1-YLOXYMETHYL SULFONIC ACID AND ANALOGS

This application is a continuation-in-part application of co-pending U.S. patent application Ser. No. 433,175, filed Oct. 6, 1982, and now abandoned.

BACKGROUND OF THE INVENTION

The β-lactam ring,

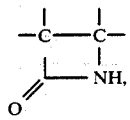

has been known since the late nineteenth century. While knowledge of β-lactam chemistry developed during the early 1900's, it was not until 1929 that Fleming reported in *Brit. J. Exper. Pathol.*, 10, 226 (1929) that a fermentation product of the organism Penicillium notatum had antibiotic properties. The compound which Fleming had worked with was benzylpenicillin,

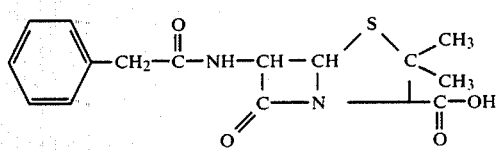

The in vivo activity of benzylpenicillin against various bacteria was reported by Chain et al. in *Lancet*, 2:226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid,

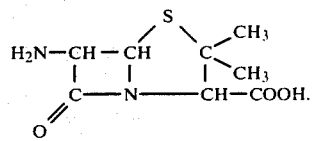

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic acid as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalsporin C,

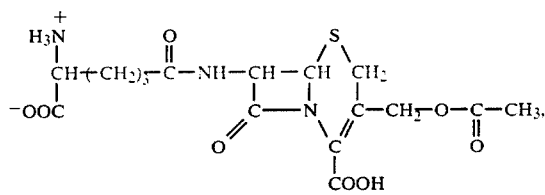

proved to be an important stepping stone in cephalosporin research. Removal of the acyl group in the 7-position of cephalosporin C yields 7-aminocephalosporanic acid,

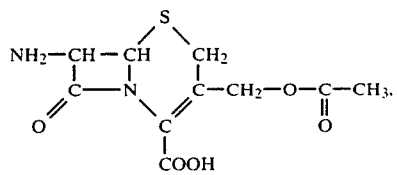

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3):122 (1972) disclose that certain actinomycete cultures isolated from soil produce antibiotics characterized by a methoxy group and D-α-aminoadipic acid on the 7-carbon of the cephem nucleus. The cephamycins, as they are known, have the formula

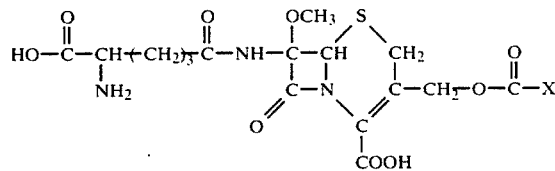

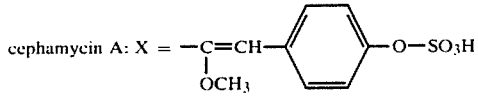

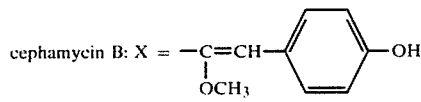

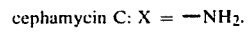

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., *The Journal of Antibiotics*, XXVIII(1):1 (1975), disclose the isolation from a fermentation broth of Streptomyces species 372A of (S)- alanyl-3-[α-(S)-chloro-3-(S)-hydroxy-2-oxo-3-azetidinyl-methyl]-(S)-alanine, which has the formula

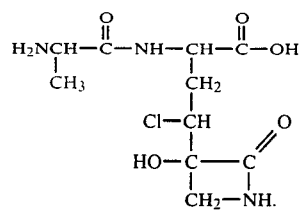

The structure of the above naturally occurring monocyclic β-lactam containing molecule is similar to the structure of the earlier discovered β-lactam containing molecules known as tabotoxins, i.e.,

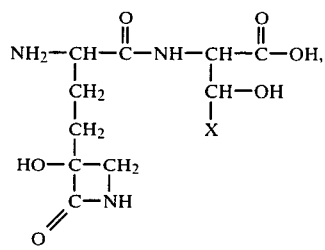

wherein X is hydrogen or methyl as reported by Stewart, *Nature*, 229:174 (1971), and Taylor et al., *Biochem. Biophys. Acta.*, 286:107 (1972).

Recently, several novel series of naturally occurring β-lactam antibiotics have been isolated. The nocardicins, nocardicin A and B, are monocyclic β-lactams having the formula

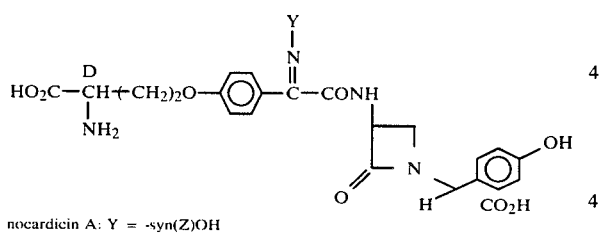

nocardicin A: Y = -syn(Z)OH
nocardicin B: Y = -anti(E)OH.

as reported by Hashimoto et al., *The Journal of Antibiotics*, XXIX (9):890 (1976).

Clavulanic acid, a bicyclic β-lactam antibiotic isolated from fermentation broths of *Streptomyces clavuligerus*, has the formula

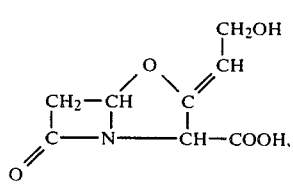

i.e., Z-(2R,5R)-3-(β-hydroxyethylidene)-7-oxo-4-oxa-1-azabicyclo[3,2,0]heptane-2-carboxylic acid, as reported by Lloyd et al., *J.C.S. Chem. Comm.*, 266 (1976).

Still another recently isolated β-lactam antibiotic is thienamycin, an antibiotic isolated from the fermentation broths of *Streptomyces cattleya*. As reported by Albers-Schonberg et al., *J.A.C.S.*, 100:20, 6491 (1978), thienamycin has the structure

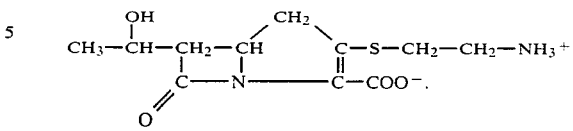

Additional fused β-lactams, olivanic acid derivatives, have recently been isolated from cultures of *Streptomyces olivaceus*. As disclosed by Brown et al., *J.C.S. Chem.Comm.*, these olivanic acid derivatives have the formulas

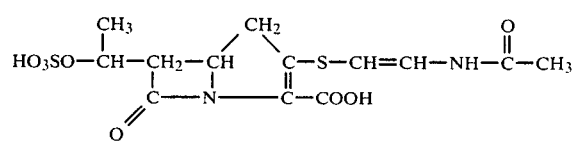

and

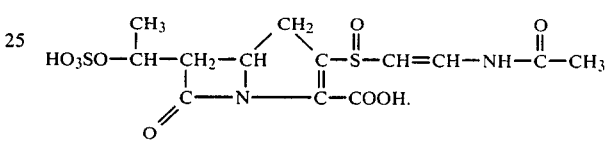

The isolation of the above antibiotics, and a discussion of their activity, is reported by Butterworth et al., *The Journal of Antibiotics*, XXXII(4):294 (1979) and by Hood et al., *The Journal of Antibiotics*, XXXII(4):295 (1979).

Another recently isolated β-lactam antibiotic is PS-5, reported by Okamura et al., *The Journal of Antibiotics*, XXXI: 480 (1978) and *The Journal of Antibiotics*, XXXIII(4):262 (1979). The structure of this antibiotic, which is produced by *Streptomyces cremeus* subspecies auratilis, is reported to be

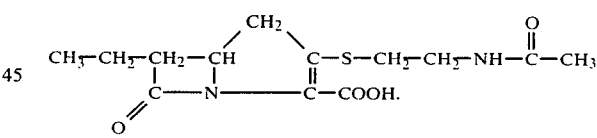

Structurally related antibiotics PS-6 and PS-7 are reported in European Patent application Ser. No. 1,567 to have the respective structures

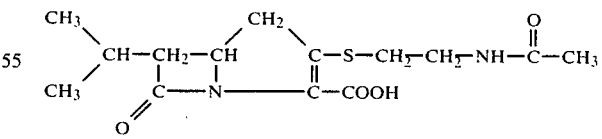

and

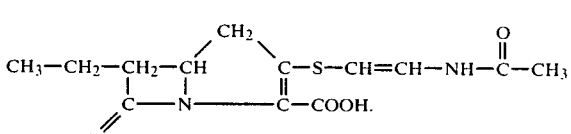

Two recently disclosed series of β-lactam antibiotics are the monocyclic β-lactams having the formulas

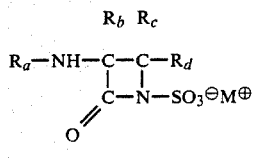

and

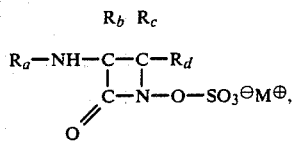

wherein $R_a$ is acyl, $R_b$ is hydrogen or alkoxy, $R_c$ and $R_d$ are various organic substituents, and $M^{\oplus}$ is a cation. The antibiotics having an $-SO_3^{\ominus}M^{\oplus}$ activating group are disclosed in United Kingdom patent application No. 2,071,650, published Sept. 23, 1981. The antibiotics having an $-O-SO_3^{\ominus}M^{\oplus}$ activating group are disclosed in European patent application No. 0051381, published May 12, 1982.

BRIEF DESCRIPTION OF THE INVENTION

This invention is directed to a novel family of β-lactam antibiotics, and to the use of such compounds as antibacterial agents. It has been discovered that the β-lactam nucleus can be biologically activated by a substituent having the formula

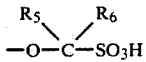

(or salt thereof) attached to the nitrogen atom in the nucleus.

β-Lactams having a

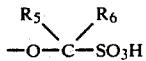

substituent (or pharmaceutically acceptable salt thereof) in the 1-position and an acylamino substituent in the 3-position exhibit activity against a range of gram-negative and gram-positive bacteria.

Illustrative members of the novel family of β-lactam antibiotics of this invention are those encompassed by the formula

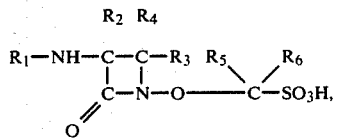

or an ester or salt thereof.

As used in formula I and throughout the specification, the symbols are as defined below.

$R_1$ is acyl;

$R_2$ is hydrogen or methoxy;

$R_3$ and $R_4$ are the same or different and each is hydrogen, alkyl, alkenyl, alkynyl, cycloalkyl, phenyl, substituted phenyl or a 4,5,6 or 7-membered heterocycle (referred to hereinafter as $R_7$) or one of $R_3$ and $R_4$ is hydrogen and the other is azido, halomethyl, dihalomethyl, trihalomethyl, alkoxycarbonyl, 2-phenylethenyl, 2-phenylethynyl, carboxyl, $-CH_2X_1$, $-S-X_2$, $-O-X_2$,

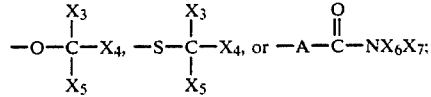

$X_1$ is azido, amino($-NH_2$), hydroxy, alkanoylamino, alkylsulfonyloxy, phenylsulfonyloxy, (substituted phenyl)sulfonyloxy, phenyl, substituted phenyl, cyano, $-S-X_2$ or $-O-X_2$;

$X_2$ is alkyl, substituted alkyl, phenyl, substituted phenyl, phenylalkyl, (substituted phenyl)alkyl, alkanoyl, substituted alkanoyl, phenylcarbonyl, (substituted phenyl)carbonyl or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

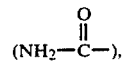

(substituted amino)carbonyl, or cyano ($-C \equiv N$);

A is $-CH=CH-$, $-CH_2-CH=CH-$, $-(CH_2)_n-$, $-(CH_2)_{n'}-O-$, $-(CH_2)_{n'}-NH-$, or $-(CH_2)_{n'}-S-CH_2$;

n is 0, 1, 2 or 3;

n' is 1 or 2.

$X_6$ and $X_7$ are the same or different and each is hydrogen or alkyl, or $X_6$ is hydrogen and $X_7$ is amino, substituted amino, acylamino or alkoxy; and $R_5$ and $R_6$ are the same or different and each is hydrogen, alkyl, alkenyl, alkynyl, phenyl, substituted phenyl, cycloalkyl or $R_7$, or $R_5$ and $R_6$ together with the carbon atom to which they are attached are cycloalkyl or $R_7$, or one of $R_5$ and $R_6$ is hydrogen and the other is azido, halomethyl, dihalomethyl, trihalomethyl, alkoxycarbonyl, 2-phenylethenyl, 2-phenylethynyl, carboxyl, $-CH_2X_1$, $-S-X_2$, $-O-X_2$, or

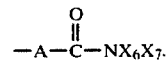

Listed below are definitions of various terms used to describe the β-lactams of this invention. These definitions apply to the terms as they are used throughout the specification (unles they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido amino($-NH_2$), halogen, hydroxy, carboxy, cyano alkoxycarbonyl, aminocarbonyl, alkanoyloxy, alkoxy, phenyloxy, (substituted phenyl)oxy, R₇-oxy, mercapto, alkylthio, phenylthio, (substituted phenyl)thio, alkylsulfinyl, or alkylsulfonyl groups.

The terms "alkanoyl", "alkenyl", "alkenyl" and "alkynyl" refers to both straight and branched chain groups. Those groups having 2 to 10 carbon atoms are preferred.

The terms "halogen" and "halo" refer to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino (—NH₂), halogen, hydroxyl, trifluoromethyl, alkyl (of 1 to 4 carbon atoms), alkoxy (of 1 to 4 carbon atoms), or carboxyl groups.

The expression "a 4,5,6 or 7-membered heterocycle" (referred to as "R₇") refers to substituted and unsubstituted, aromatic and non-aromatic groups containing one or more nitrogen, oxygen or sulfur atoms. Exemplary substituents are oxo(=O), halogen, hydroxy, nitro, amino, cyano, trifluoromethyl, alkyl of 1 to 4 carbons, alkoxy of 1 to 4 carbons, alkylsulfonyl, phenyl, substituted phenyl, and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-furanyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NY₁Y₂ wherein Y₁ is hydrogen, alkyl, phenyl, substituted phenyl, phenylalkyl or (substituted phenyl)alkyl, and Y₂ is alkyl, phenyl, substituted phenyl, phenylalkyl, (substituted phenyl)alkyl, hydroxy, cyano, alkoxy, phenylalkoxy, or amino (—NH₂).

The term "substituted alkanoyl" includes within its scope compounds having the formula (substituted alkyl)

(wherein "substituted alkyl" is defined above) and phenylalkanoyl.

The term "acyl" refers to all organic radicals derived from an organic acid (i.e., a carboxylic acid) by removal of the hydroxyl group. Certain acetyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

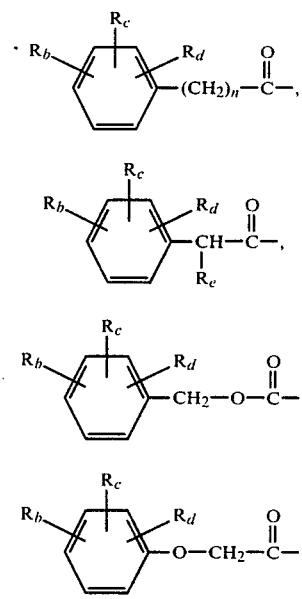

-continued

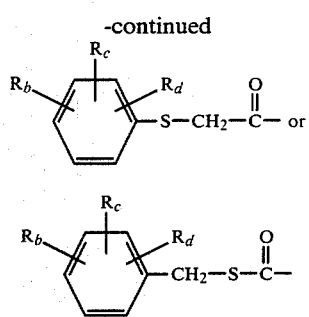

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

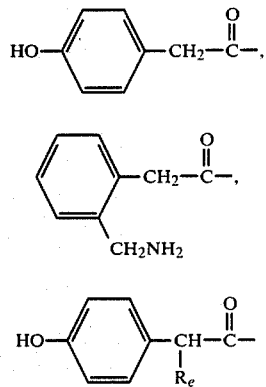

($R_e$ is preferably a carboxyl salt or sulfo salt) and

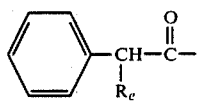

($R_e$ is preferably a carboxyl salt or sulfo salt).

(c) Heteroaromatic groups having the formula

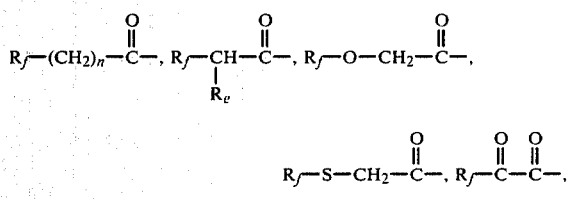

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

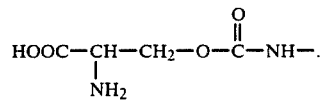

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

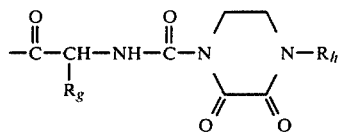

wherein $R_g$ is an aromatic group (including carbocyclic aromatics such as those of the formula

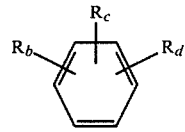

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., $-N=CH-R_g$ wherein $R_g$ is as defined above), arylcarbonylamino (i.e., $$-NH-\overset{O}{\underset{\|}{C}}-R_g$$

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula $$-\overset{O}{\underset{\|}{C}}-\underset{R_g}{C}=N-O-R_i$$

wherein $R_g$ is as defined above and $R_i$ is hydrogen, $R_c$, alkyl, cycloalkyl, alkylaminocarbonyl, arylaminocarbonyl (i.e.,

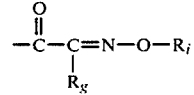

wherein $R_g$ is as defined above) or substituted alkyl (wherein the alkyl group is substituted with 1 or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_1$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

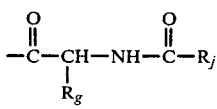

wherein $R_g$ is as defined above and $R_j$ is

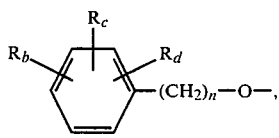

amino, alkylamino, (cycloalkyl)amino, amido, alkylamido, (cyanoalkyl)amido,

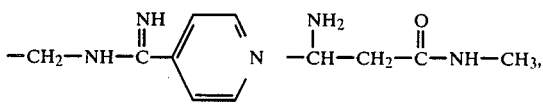

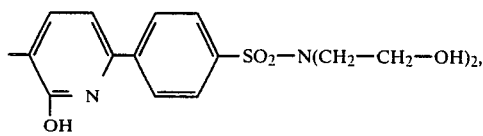

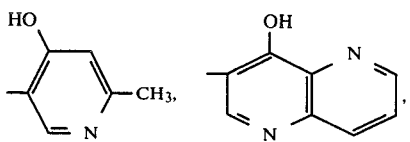

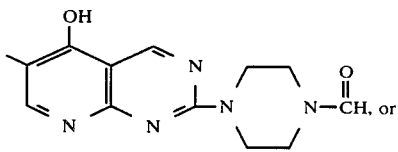

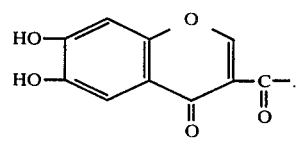

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

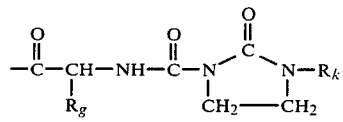

wherein $R_g$ is as defined above and $R_k$ is hydrogen, alkylsulfonyl, arylmethyleneamino (i.e., $—N{=}CH—R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts" refer to basic salts formed with inorganic and organic bases. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

β-Lactams having a

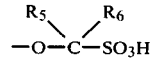

substituent (or salt thereof) in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins, (e.g., cephamycin C).

With respect to the preferred β-lactams of formula I, the structural formulas have been drawn to show the stereochemistry at the chiral center in the 3-position.

Also included within the scope of this invention are racemic mixtures which contain the above-described β-lactams.

DETAILED DESCRIPTION OF THE INVENTION

β-Lactams having a

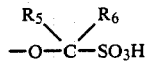

substituent (or salt thereof) in the 1-position of the β-lactam nucleus and an acylamino substituent in the 3-position of the β-lactam nucleus have activity against a range of gram-negative and gram-positive organisms. The

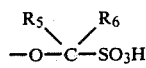

substituent (or salt thereof) is essential to the activity of the compounds of this invention.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The β-lactams of this invention can be prepared from an amino acid having the formula

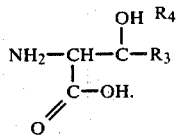

The amino group is first protected with a classical protecting group (e.g., t-butoxycarbonyl), benzyloxycarbonyl, o-nitrophenylsulfenyl, etc.), yielding a compound having the formula

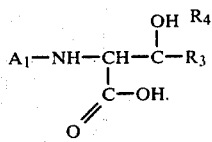

In formula III, and throughout the specification, the symbol "A₁" refers to a nitrogen protecting group.

The carboxyl group of a protected amino acid of formula III is then reacted with an amine having the formula

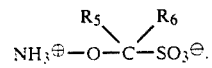

The reaction proceeds in the presence of a coupling agent such as 1-ethyl-3-(3-dimethylaminopropyl)carbodiimide or dicyclohexylcarbodiimide, and yields a salt of the compound having the formula

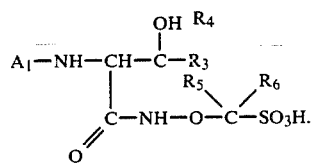

The hydroxyl group of a compound of formula V (or a salt thereof) is converted to a leaving group, using, for example, a classical reagent such as methanesulfonyl chloride (methanesulfonyl is referred to hereinafter as "Ms").

The fully protected compound having the formula

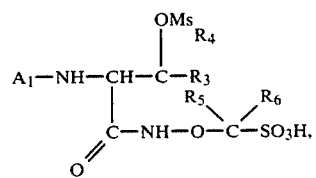

or a salt thereof, is cyclized by treatment with base, e.g., potassium carbonate. The reaction is preferably carried out in an organic solvent such as acetone, under reflux conditions, and yields a compound having the formula

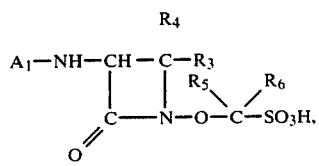

or a salt thereof.

Alternatively, cyclization of a compound of formula V can be accomplished without first converting the hydroxyl group to a leaving group. Treatment of a compound of formula V (or a salt thereof) with triphenylphosphine and diethylazodicarboxylate or carbon tetrachloride and triethylamine, yields a compound of formula VII.

Both of the methods disclosed above for ring closure of a compound of formula V result in the invention of the stereochemistry at the carbon bonded to the R₃ and R₄ substituents.

Deprotection of the 3-amino substituent of a compound of formula VII can be accomplished using art-recognized techniques. If, for example, the protecting group is t-butoxycarbonyl, trifluoroacetic acid can be used to deprotect the amino group. If the protecting group is benzyloxycarbonyl, catalytic (e.g., palladium on charcoal) hydrogenation can be used. If the protecting group is o-nitrophenylsulfenyl, p-toluenesulfonic acid can be used in combination with p-thiocresol. The deprotected compound has the formula

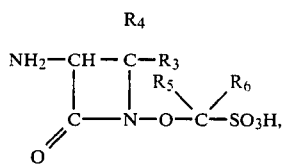 VIII or a salt thereof, and is a key intermediate for preparing the compounds of this invention. The compounds of formula VIII form an integral part of this invention.

Well known acylation techniques can be used to convert a compound of formula VIII to the corresponding compound having the formula

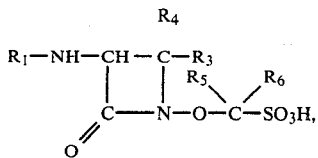 IX or a salt thereof. Exemplary techniques include reaction with a carboxylic acid ($R_1$-OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group ($R_1$) contains reactive functionality (such as amino or carboxyl groups) it may be necessary to first protect these functional groups, then carry out the acylation reaction, and finally deprotect the resulting product.

The products of formula I wherein $R_2$ is methoxy can be prepared from the corresponding compound of formula VII wherein $A_1$ is benzyloxycarbonyl. Halogenating (preferably chlorinating) the amide nitrogen of a compound of formula VII ($A_1$ is benzyloxycarbonyl) yields a compound having the formula

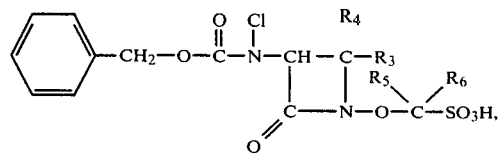 X or a salt thereof. Reagents and procedures of N-chlorinating amides are known in the art. Exemplary reagents are tert.-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of a compound of formula X with a methoxylating agent, e.g., an alkali metal methoxide, yields a compound (in combination with its enantiomer if $R_3$ and $R_4$ are the same or if X is a racemic mixture) having the formula

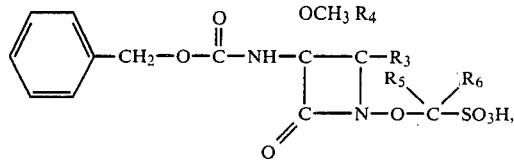 XI or a salt thereof. The reaction can be run in an organic solvent, e.g., a polar organic solvent such as tetrahydrofuran, at a reduced temperature.

Alternatively, a compound of formula VII, wherein $A_1$ is benzyloxycarbonyl, can be converted to a compound of formula XI using a single step procedure. The methoxylating agent can first be mixed with a compound of formula VII ($A_1$ is benzyloxycarbonyl) and the N-chlorinating reagent then added to the reaction mixture.

Conversion of a compound of formula XI to the desired products of formula I can be accomplished using the procedures described above for the conversion of an intermediate of formula VII to a product of this invention.

The starting materials of formula II are readily obtainable using art-recognized procedures; see, for example *Synthesis*, pg. 216 (1979) and *J. Org. Chem.*, 44:3967 (1979).

The following examples are specific embodiments of this invention.

EXAMPLE 1

[3S-[3α(Z),4β]]-2-[[[1-(2-Amino-4-thiazolyl)-2-[[4-methyl-2-oxo-1-(sulfomethoxy)-3-azetidinyl]amino]-2-oxoethylidene]amino]oxy]-2-methylpropanoic acid, dipotassium salt (A) Aminoxymethanesulfonic acid Acetone oxime (1.46 g, 20 mmole) was added to a suspension of a 60% mineral oil dispersion of sodium hydride (0.8 g, 20 mmole) in 16 ml of dry dimethylsulfoxide. This was followed by the portionwise addition of sodium bromomethane sulfonate (3.94 g, 20 mmole). The reaction was heated at 90°–95° C. for 4 hours under nitrogen, cooled and washed twice with 250 ml of ether. Product solidified, was washed with 100 ml of dichloromethane, filtered and dried over $P_2O_5$ to yield 15.3 g of crude material. This was dissolved in 20 ml of water, and tetrabutylammonium hydrogen sulfate (7.5 g, 22 mmole) was added. The resulting ion paired product was extracted twice with 200 ml of dichloromethane. The dichloromethane solution was dried ($Na_2SO_4$, and concentrated in vacuo. Hydrolysis of the acetone oxime was accomplished by heating in 120 ml of 2N HCl at 130° C. for 4 hours. This solution was concentrated in vacuo from water twice and then from acetonitrile. The product solidified upon addition of dichloromethane, and was filtered and dried in vacuo to yield 2.5 g of the title compound.

(B) O-Sulfomethyl-α-N-t-butoxycarbonyl-L-threonine hydroxamate, potassium salt

Aminoxymethanesulfonic acid (1.14 g, 8.9 mmole) was added to a solution of t-butoxycarbonyl-L-threonine (1.96 g, 8.9 mmole) in 16 ml of water and 4 ml of tetrahydrofuran at 0° C. The pH was adjusted to 4.5 with 1N KOH, and 1-ethyl-3-(3-dimethylaminopropyl)-carbodiimide hydrochloride (1.87 g, 9.7 mmole) in 8 ml of water was added dropwise. The reaction mixture was stirred at ambient temperature for 2 hours, and during this time, the pH was maintained at 4 to 4.5 by occasional addition of 1N $H_2SO_4$. The product was ion paired with tetrabutylammonium hydrogensulfate (3.05 g, 8 mmole) at pH 2.8 and extracted from the aqueous solution with four 100 ml portions of dichloromethane. The dichloromethane solution was dried ($Na_2SO_4$) and concentrated in vacuo to yield 4.5 g of product as the tetrabutylammonium salt. This was converted to the potassium salt by ion exchange on 150 ml of Dowex 50×(0.7 meq $K^{\oplus}$/ml), and after lyophilization, 2.63 g of the title compound was obtained.

(C)
O-Sulfomethyl-α-N-t-butoxycarbonyl-L-(O-methanesulfonylthreonine)hydroxamate, tetrabutylammonium salt To a partial solution of O-sulfomethyl-α-N-t-butoxycarbonyl-L-threonine hydroxamate, potassium salt (2.37 g, 6.5 mmole) in 50 ml of dry pyridine at 0°–5° C. under nitrogen was added dropwise 0.8 ml (excess) of methanesulfonyl chloride. The reaction was stirred at room temperature for 4 hours, and then concentrated in vacuo. The residue was dissolved in 10 ml of water, and 2.0 g (6 mmole) of tetrabutylammonium hydrogensulfate was added at pH 2.8. The ion paired material was extracted with chloroform. The chloroform was dried and concentrated in vacuo to yield 2.6 g of crude product.

(D)
[3S-(3α,4β)]-3-[[(1,1-Dimethylethoxy)carbonyl]amino]-4-methyl-2-oxo-1-(sulfomethoxy)azetidine, potassium salt O-Sulfomethyl-α-N-t-butoxycarbonyl-L-(O-methanesulfonylthreonine)hydroxamate, tetrabutylammonium salt (2.6 g, 4.0 mmole) was dissolved in 5 ml of acetone and added dropwise to a refluxing suspension of 2.2 g of potassium carbonate in 65 ml of acetone. Refluxing was continued for 3.5 hours and the reaction was cooled, filtered, and concentrated in vacuo. The residue was dissolved in 10 ml of 0.5M pH 5.5 $KH_2PO_4$, and the pH was adjusted to 2.8. Product was extracted four times with 100 ml portions of dichloromethane, and the combined extract was dried and concentrated in vacuo to yield 1.52 g of crude tetrabutylammonium ion paired β-lactam salt. The potassium salt was obtained by ion exchange through 50 ml of Dowex 50×(0.7 meq $K^{\oplus}$/ml) to yield upon lyophilization 0.53 g of crude material, which was further purified by chromatography through 100 ml of HP-20 using water. The appropriate fractions were combined and lyophilized to yield 0.245 g of product.

Analysis Calc'd for $C_{10}H_{17}N_2O_7SK \cdot 1.2H_2O$: C, 32.46; H, 5.28; N, 7.57; S, 8.66; Found: C, 32.52; H, 4.76; N, 7.43; S, 8.30.

(E)
[3S-(3α,4β)]-1-Sulfomethoxy-3-amino-4-methyl-2-oxo-1-azetidine

[3S-(3α,4β)]-3-[[(1,1-Dimethylethoxy)carbonyl]amino]-4-methyl-2-oxo-1-(sulfomethoxy)azetidine, potassium salt (0.245 g, 0.68 mmole) was suspended in 0.5 ml of dichloromethane and 0.5 ml of anisole. The reaction mixture was cooled to 0° C., and trifluoroacetic acid (1.0 ml) was added under nitrogen. The reaction mixture was stirred for 1 hour and then concentrated in vacuo to a residue which was evaporated from benzene twice. This was triturated with ether, and the ether was decanted to give the desired product as a white solid.

(F)
[3S-[3α(Z),4β]]-2-[[[1-(2-Amino-4-thiazolyl)-2-[[4-methyl-2-oxo-1-(sulfomethoxy)-3-azetidinyl]amino]-2-oxoethylidene]amino]oxy]-2-methylpropionic acid, diphenylmethyl ester, potassium salt (Z)-2-Amino-α-[[2-(diphenylmethoxy)-1,1-dimethyl-2-oxoethoxy]-imino]-4-thiazoleacetic acid (0.30 g, 0.68 mmole) and 1-hydroxybenzotriazole hydrate (0.10 g, 0.68 mmole) were dissolved in 4 ml of dry dimethylformamide under nitgoren. This was cooled to 0° C., and N,N'-dicyclohexylcarbodiimide (0.14 g, 0.68 mmole) was added portionwise. After addition, the reaction was stirred at 0° C. for 1 hour. To this was added a solution of the above crude 3-amino-1-(sulfomethoxy)azetidine (ca. 0.68 mmole) in 10 ml of dimethylformamide and 0.5 ml of N,N-diisopropylethylamine at 0° C. The reaction was stirred at 0° C. for 1 hour and then at room temperature overnight. The solution was filtered, and the filtrate was concentrated in vacuo. The residue was dissolved in 50 ml of dichloromethane and washed with 2 ml of water. Upon evaporation of dichloromethane, 0.372 g of crude product was obtained. This was passed through 30 ml of Dowex 50 (0.7 meq $K^{\oplus}$/ml) using water, to yield upon lyophilization 0.211 g of crude product, contaminated with hydroxybenzotriazole.

(G)
[3S-[3α(Z),4β]]-2-[[[1-(2-Amino-4-thiazolyl)-2-[[4-methyl-2-oxo-1-(sulfomethoxy)-3-azetidinyl]amino]-2-oxoethylidene]amino]oxy]-2-methylpropanoic acid, dipotassium salt

[3S-[3α(Z),4β]]-2-[[[1-(2-Amino-4-thiazolyl)-2-[[4-methyl-2-oxo-1-(sulfomethoxy)-3-azetidinyl]amino]-2-oxoethylidene]amino]oxy]-2-methylpropionic acid, diphenylmethyl ester, potassium salt (0.211 g) was dissolved in 1.8 ml of dichloromethane, 0.5 ml of anisole, and 1.5 ml of trifluoroacetic acid, and stirred under nitrogen at 0° C. for 2 hours. The reaction mixture was condentrated in vacuo and evaporated from benzene twice. The residue was washed with ether: ethyl acetate (1:1) and with ether:acetonitrile (1:1) to give a white solid. This was dissolved in 1.0 ml of pH 5.5 0.5M $KH_2PO_4$, adjusted to pH 6.5 with 1N KOH, and chromatographed through 40 ml of HP-20 with water to give 53 mg of the title compound, melting point 200° C., dec.

Analysis Calc'd for $C_{14}H_{17}N_5O_9S_2K_2 \cdot 2.75H_2O$: C, 28.44; H, 3.84; N, 11.85; S, 10.84; Found: C, 28.32; H, 3.36; N, 11.90; S, 10.37.

EXAMPLE 2
[3S-[3α(R),4β]]-[[3-[[[[(4-Ethyl-2,3-dioxo-1-piperazinyl)carbonyl]amino]phenylacetyl]amino]-4-methyl-2-oxo-1-azetidinyl]oxy]methanesulfonic acid, monopotassium salt To a solution of (R)-α-[[(4-ethyl-2,3-dioxo-1-piperazinyl)carbonyl]amino]phenylacetic acid (160 mg, 0.5 mM) and N-hydroxybenzotriazole (77 mg, 0.5 mM) in dimethylformamide (2.5 ml), dicyclohexylcarbodiimide (103 mg, 0.5 mM) was added at 0° C. The reaction mixture was stirred at 0°–5° C. for 30 minutes when a solution of [3S-(3α,4β)]-1-sulfomethoxy-3-amino-4- methyl-2-oxo-1-azetidine in dimethylformamide (2 ml) was added followed by the addition of ethyldiisopropylamine (0.5 ml, 3 mM); the reaction mixture was stirred at room temperature overnight. The precipitate was removed by filtration and the solvent removed in vacuo. The residue was taken into 0.5M monobasic potassium phosphate (10 ml) (pH 5.6), filtered again, and the clear solution adjusted to pH 5.9 with 1N potassium hydroxide. The solution was passed through a Diaion HP-20 column (1.5×27 cm) and the column eluted with water and then with a mixture of acetonitrile:water (1:9) to obtain 80 mg of impure title compound. The entire amount was passed again through a Diaion HP-20 column (2.5×27 cm) and eluted with water and acetonitrile:water (1:9) which eluted 50 mg of the desired compound with about 20–30% impurity. After the product was rechromatographed through a Diaion HP-20 column (1.5×25 cm) and the column eluted with water first and then with acetontrile:water (1:9), compound of satisfactory purity was eluted. Yield: 32 mg. The NMR spectrum and the microanalysis indicated that the final product was present as the ethyldiisopropylamine salt; 24 mg was passed through an ion exchange column (1×10 cm, Bio-Rad AG50Wx2, K-cycle) and the title compound eluted with water. Yield: 19 mg.

Calc'd. for $C_{20}H_{24}N_5O_9SK(549.6).1.6H_2O$ (578.38): C, 41.53; H, 4.74; N, 12.11; S, 5.54; Found: C, 41.53; H, 4.46; N, 11.13; S, 5.61.

EXAMPLE 3

[3S-[3α(Z),4β]]-[[3-[[(2-Amino-4-thiazolyl)(methoxyimino)acetyl]amino]-4-methyl-2-oxo-1-azetidinyl]oxy]methanesulfonic acid, monopotassium salt To a solution of (Z)-2-amino-α-(methoxyimino)-4-thiazoleacetic acid (101 mg; 0.5 mM) in dimethylformamide (2 ml), N-methylmorpholine (0.055 ml; 0.55 mM) was added at −15° C. followed by the addition of diphenylchlorophosphate (0.1 ml; 0.5 mM) with stirring and while maintaining the temperature of −15° C. After 15 minutes a solution of [3S-(3α,4β)]-1-sulfomethoxy-3-amino-4-methyl-2-oxo-1-azetidine in dimethylformamide (2 ml) and N-methylmorpholine (0.055 ml, 0.5 mM) was added. The reaction mixture was stirred at −15° C. for 15 minutes and then at room temperature for 2 hours. The solvent was removed in vacuo, the residue dissolved in water (3 ml) and the pH was adjusted with 1N potassium hydroxide. The solution was passed through a Diaion HP-20 column (2.5×27 cm, 7 ml/tube) and the column eluted first with five column volumes of water and then with acetonitrile:water (1:9) to obtain 80 mg of the desired product. The brownish color of the product was removed by dissolving the compound in water (3 ml) and slightly warming the solution with Darco G-60. After the charcoal was removed by filtration through Celite, the solvent was removed in vacuo and the residue treated several times with acetonitrile, removing the acetonitrile each time in vacuo. Yield: 57 mg.

Calc'd. for $C_{11}H_{14}N_5O_7S_2K.0.1CH_3CN$: C, 38.11; H, 4.82; N, 15.92; S, 12.56; Found: C, 37.94; H, 5.36; N, 15.92; S, 12.56.

EXAMPLE 4

[3S-[3α(Z),4α]]-[[3-[[(2-Amino-4-thiazolyl)(methoxyimino)acetyl]amino]-4-methyl-2-oxo-1-azetidinyl]oxy]methanesulfonic acid, monpotassium salt (A) O-Sulfomethyl-α-N-t-butoxycarbonyl-allothreonine hydroxamate, potassium salt To a solution of t-butoxycarbonyl-allothreonine (6.04 g; 27.5 mM) in 1N potassium hydroxide (27.5 ml), a solution of aminoxymethane sulfonic acid (3.5 g; 27.5 mM) in water (65 ml) was added. The temperature of the clear solution was lowered to about 5° C. and a solution of 1-ethyl-3-(3-dimethylaminopropyl)carbodiimide (5.8 g, 30.25 mM) in water (25 ml) was added. The reaction mixture was stirred at room temperature for two hours maintaining the pH at 4.5. The title compound was isolated from the reaction mixture by the formation of an ion pair with tetrabutylammonium sulfate (9.4 g; 2.75 mM) and the tetrabutylammonium salt of the title compound was extracted with dichloromethane. The extract was dried over sodium sulfate and the solvent removed in vacuo. Yield: 10 g. The entire amount was dissolved in water (20 ml) and the solution passed through an ion exchange column (Bio-Rad AG50Wx2, K-cycle); the title compound eluted with water. Yield: 5.7 g.

(B) O-Sulfomethyl-α-N-t-butoxycarbonyl-allo-(O-methanesulfonylthreonine)hydroxamate, tetrabutyl ammonium salt To a solution of O-sulfomethyl-α-N-t-butoxycarbonyl-allo-threonine hydroxamate, potassium salt (5.2 g; 14.2 mM) in dry pyridine (100 ml), methanesulfonyl chloride (1.77 ml; 22.7 mM) was added dropwise at 0°–5° C. Upon completion of the addition, the ice bath was removed and the reaction mixture was stirred at room temperature for 4 hours. The solvent was removed in vacuo, the residue was dissolved in water (50 ml) and the title compound was ion paired with tetrabutylammonium sulfate (4.8 g; 14.2 mM) at pH 2.8 and then extracted with dichloromethane. The extract was dried over sodium sulfate and the solvent removed in vacuo. The residue was dissolved in water, the solution passed through an ion exchange column (Bio-Rad AG50Wx2, K-cycle), the product eluted with water and the solution lyophilized. The light powder (4.3 g) was dissolved in water (50 ml) and Bio-Rad AG50Wx2 (tetrabutylammonium sulfate-75 ml) was added to the solution, and the suspension stirred for 30 minutes at room temperature. After removal of the resin by filtration, the title compound was obtained by the lyophilization of the filtrate. Yield: 4.2 g.

(C) [3S-(3α,4α)]-3-[[(1,1-Dimethylethoxy)carbonyl]amino]-4-methyl-2-oxo-1-(sulfomethoxy)azetidine, potassium salt To a refluxed suspension of potassium carbonate (3.84 g, 27.8 mM) in acetone (115 ml) a solution of O-sulfomethyl-α-N-t-butoxycarbonylallo-(O-methanesulfonylthreonine)hydroxamate, tetrabutylammonium salt (3.2 g, 4.9 mM) in acetone (22 ml) was added. The suspension was refluxed for a total of 3.5 hours. After cooling, the suspension was filtered and the acetone was removed from the filtrate in vacuo. The residue was dissolved in 0.5M monobasic potassium phosphate (25 ml, pH 5.6) and the pH value lowered to 2.8 with 1N sulfuric acid. The tetrabutylammonium salt was extracted with dichloromethane and the solvent was removed in vacuo. The residue was dissolved in water and the solution stirred with Bio-Rad AG50Wx2 (potassium cycle, 35 ml), resin for 30 minutes. The resin was removed by filtration and the title compound was obtained by lyophilization of the aqueous solution. Yield: 1.1 g.

(D)

[3S-(3α,4α)]-3-Amino-4-methyl-2-oxo-1-(sulfomethoxy)azetidine

Following the procedure of example 1E, but substituting [3S-(3α,4α)]-3-[[(1,1-dimethylethoxy)carbonyl]amino]-4-methyl-2-oxo-1-(sulfomethoxy)azetidine, potassium salt for [3S-(3α,4β)]-3-[[(1,1-dimethylethoxy)carbonyl]amino-4-methyl-2-oxo-1-(sulfomethoxy)azetidine, potassium salt, yielded the title compound.

(E)

[3S-[3α(Z),4α]]-[[3-[[(2-Amino-4-thiazolyl)(methoxyimino)acetyl]amino]-4-methyl-2-oxo-1-azetidinyl]oxy]methanesulfonic acid, monpotassium salt To a solution of (Z)-2-amino-α-(methoxyimino)-4-thiazoleacetic acid (169 mg, 0.84 mM) in dimethylformamide (5 ml), triethylamine (0.12 ml, 0.84 mM) was added at −15° C. Diphenylchlorophosphate (0.17 ml, 0.84 mM) was added with stirring and the temperature of −15° C. was maintained for 30 minutes. To the reaction mixture, a solution of [3S-(3α,4α)]-3-amino-4-methyl-2-oxo-1-(sulfomethoxy)azetidine in dimethylformamide (2.5 ml) and triethylamine (0.12 ml, 0.84 mM) was added. The stirring was continued for 30 minutes at the same temperature and then at room temperature overnight. The solvent was removed in vacuo and the residue dissolved in water (5 ml); the pH of the solution was adjusted to 5.9 with 1N potassium hydroxide. The solution was applied to a Diaion HP-20 column (2.5×14 cm) and the column eluted with water to obtain 78 mg of the desired compound.

Calc'd. for $C_{11}H_{14}N_5O_7S_2K \cdot 0.25H_2O$ (436.41): C, 30.27; H, 3.35; N, 16.05; S, 14.70; K, 8.96 Found: C, 30.53; H, 3.54; N, 15.80; S, 14.46; K, 8.72.

EXAMPLE 5

[3S-[3α(Z),4α]]-2-[[[1-(2-Amino-4-thiazolyl)-2-[[4-methyl-2-oxo-1-(sulfomethoxy)-3-azetidinyl]amino]-2-oxoethylidine]amino]oxy]-2-methylpropanoic acid, dipotassium salt To a solution of (Z)-2-amino-α-[[2-(diphenylmethoxy)-1,1-dimethyl-2-oxoethoxy]imino]-4-thiazoleacetic acid (369 mg; 0.84 mM) in dimethylformamide (5 ml), triethylamine (0.118 ml; 0.84 mM) was added at −15° C., followed by the addition of diphenylchlorophosphate (0.174 ml; 0.84 mM). The reaction mixture was stirred for 25 minutes at the same temperature, and a solution of [3S-(3α,4α)]-3-amino-4-methyl-2-oxo-1-(sulfomethoxy)azetidine in dimethylformamide (2.5 ml) and triethylamine (0.12 ml; 0.884 mM) was added. The pH of 3.5-4 was maintained during the coupling reaction with triethylamine. The reaction was carried out at −15° C. for 25 minutes and at room temperature overnight. The precipitate was filtered off and the solvent was removed in vacuo. The residue was dissolved in 50% acetonitrile:water and the solution obtained was passed through an ion exchange column (Bio-Rad AG50Wx2). The column was eluted with the same mixture of solvents. The fractions containing [3S-[3-α(Z),4α]]-2-[[[1-(2-amino-4-thiazolyl)-2-[[4-methyl-2-oxo-1-(sulfomethoxy)-3-azetidinyl]-amino]-2-oxoethylidine]amino]oxy]-2-methylpropanoic acid, diphenylmethyl ester, potassium salt were combined, the solvents removed in vacuo and the residue dried thoroughly in vacuo over platinum oxide. Yield: 100 mg.

The entire amount was dissolved in dichloromethane (2 ml) and anisole (0.5 ml) and the solution was cooled to −15° C. at which temperature triethylamine (2 ml) was added. The clear solution was stirred at −15° C. for one hour, the solvents removed in vacuo and the residue was washed with ether several times. The dry residue was dissolved in water and the pH of the solution was adjusted to about 5 with 1N potassium hydroxide. The obtained solution was applied to an HP-20 column (1.5×24 cm) and the desired product eluted from the column with water. Yield: 12.5 mg. Mass spectroscopic analysis (fast atom bombardment) revealed the molecular ions +466 and −464 (title compound as a free acid).

Additional compounds falling within the scope of this invention are:

(3S-trans)-[[[(2-Amino-4-thiazolyl)[[(2,2,2-trifluoroethoxy)imino]acetyl]amino]-4-methyl-2-oxo-1-azetidinyl]oxy]methanesulfonic acid, monopotassium salt (3S-trans)-[[[(2-Amino-4-thiazolyl)[[(2-amino-2-oxoethoxy)imino]acetyl]amino]-4-methyl-2-oxo-1-azetidinyl]oxy]methanesulfonic acid, monopotassium salt (3S-trans)-[[[(2-Amino-4-thiazolyl)[[(carboxymethoxy)imino]acetyl]amino]-4-methyl-2-oxo-1-azetidinyl]-oxy]methanesulfonic acid, dipotassium salt (3S-trans)-[[[(2-Amino-4-thiazolyl)[[[(1carboxycyclopropyl)oxy]imino]acetyl]amino]-4-methyl-2-oxo-1-azetidinyl]-oxy]methanesulfonic acid, dipotassium salt

[3S-[3α(R),4β]]-[[3-[(Aminophenylacetyl)amino]-4-methyl-2-oxo-1-azetidinyl]oxy]methanesulfonic acid, monopotassium salt (3S-trans)-[[3-[(Phenylacetyl)amino]-4-methyl-2-oxo-1-azetidinyl]oxy]methanesulfonic acid, monopotassium salt (3S-trans)-[[3-[(2-Thienylacetyl)amino]-4-methyl-2-oxo-1-azetidinyl]oxy]methanesulfonic acid, monopotassium salt (3S-trans)-[[3-[[(2,6-Dimethoxyphenyl)acetyl]amino]-4-methyl-2-oxo-1-azetidinyl]oxy]methanesulfonic acid, monopotassium salt

[3S-[3α(S),4β]]-[[3-[[[(Aminocarbonyl)amino]-2-thienylacetyl]amino]-4-methyl-2-oxo-1-azetidinyl]oxy]methanesulfonic acid, monopotassium salt

[3S-[3α(R),4β]]-[[3-[(Carboxyphenylacetyl)amino]-4-methyl-2-oxo-1-azetidinyl]oxy]methanesulfonic acid, dipotassium salt

[3S-[3α(±),4β]]-[[3-[(Phenylsulfoacetyl)amino]-4-methyl-2-oxo-1-azetidinyl]oxy]methanesulfonic acid, dipotassium salt (3S-trans)]-[[3-[[(2-Amino-4-thiazolyl)oxoacetyl]amino]-4-methyl-2-oxo-1-azetidinyl]oxy]methanesulfonic acid, monopotassium salt

[3S-[3α(R),4β]]-[[3-[[[[2-Oxo-3-[(phenylmethylene)amino]-1-imidazolidinyl]carbonyl]amino]phenylacetyl]amino]-4-methyl-2-oxo-1-azetidinyl]oxy]methanesulfonic acid, monopotassium salt

[3S-[3α(Z),4β]]-[[3-[[2-Furanyl(methoxyimino)acetyl]amino]-4-methyl-2-oxo-1-azetidinyl]oxy]methanesulfonic acid, monopotassium salt

[3S(Z)]-[[3-[[(2-Amino-4-thiazolyl)(methoxyimino)acetyl]amino]-2-oxo-1-azetidinyl]oxy]methanesulfonic acid, monopotassium salt

[3S(Z)]-[[3-[[(2-Amino-4-thiazolyl)[(1-carboxy-1-methylethoxy)imino]acetyl]amino]-2-oxo-1-azetidinyl]oxy]methanesulfonic acid, dipotassium salt

[3S(Z)]-[[3-[[(2-Amino-4-thiazolyl)[(2,2,2-trifluoroethoxy)imino]acetyl]amino]-2-oxo-1-azetidinyl]oxy]methanesulfonic acid, monopotassium salt

[3S(Z)]-[[3-[[(2-Amino-4-thiazolyl)[(2-amino-2-oxoethoxy)imino]acetyl]amino]-2-oxo-1-azetidinyl]oxy]methanesulfonic acid, monopotassium salt

[3S-[3α(S),4β]]-[[3-[[[(Aminocarbonyl)amino]-2-thienylacetyl]amino]-4-methyl-2-oxo-1-azetidinyl]oxy]methanesulfonic acid, monopotassium salt

[3S-[(3α(±),4β]]-[[3-[(Phenylsulfoacetyl)amino]-4-methyl-2-oxo-1-azetidinyl]oxy]methanesulfonic acid, dipotassium salt

[3S-[3α(R),4β]]-[[3-[[[[(4-Ethyl-2,3-dioxo-1-piperazinyl)carbonyl]amino]phenylacetyl]amino]-4-methyl-2-oxo-1-azetidinyl]oxy]methanesulfonic acid, monopotassium salt

[3S(Z)]-[[3-[(Phenoxyacetyl)amino]-2-oxo-1-azetidinyl]oxy]methanesulfonic acid, monopotassium salt (3S-cis)-[[[(2-Amino-4-thiazolyl)[[(2,2,2-trifluoroethoxy)imino]acetyl]amino]-4-methyl-2-oxo-1-azetidinyl]oxy]methanesulfonic acid, monopotassium salt (3S-cis)-[[[(2-Amino-4-thiazolyl) [[[carboxymethoxy)imino]acetyl]amino]-4-methyl-2-oxo-1-azetidinyl]oxy]methanesulfonic acid, dipotassium salt (3S-cis)-[[[(2-Amino-4-thiazolyl)[[[(1-carboxycyclopropyl)oxy]imino]acetyl]amino]-4-methyl-2-oxo-1-azetidinyl]oxy]methanesulfonic acid, dipotassium salt (3S-cis)-[[[(2-Amino-4-thiazolyl)[[(2-amino-2-oxoethoxy)imino]acetyl]amino]-4-methyl-2-oxo-1-azetidinyl]oxy]methanesulfonic acid, monopotassium salt

[3S-[3α(R),4α]]-[[3-[(Carboxyphenylacetyl)amino]-4-methyl-2-oxo-1-azetidinyl]oxy]methanesulfonic acid, dipotassium salt

[3S-[3α(R),4α]]-[[3-[[[[(4-Ethyl-2,3-dioxo-1-piperazinyl)carbonyl]amino]phenylacetyl]amino]-4-methyl-2-oxo-1-azetidinyl]oxy]methanesulfonic acid, monopotassium salt

[3S-[3α(S),4α]]-[[3-[[[(Aminocarbonyl)amino]-2-thienylacetyl]amino]-4-methyl-2-oxo-1-azetidinyl]oxy]methanesulfonic acid, monopotassium salt

[3S-[3α(R),4α]]-[[3-[(Aminophenylacetyl)amino]-4-methyl-2-oxo-1-azetidinyl]oxy]methanesulfonic acid, monopotassium salt

[3S-[3α(Z),4β]]-[[3-[[(2-Amino-4-thiazolyl)[(1-carboxy-1-methylethoxy)imino]acetyl]amino]-4-[[(aminocarbonyl)oxy]methyl]-2-oxo-1-azetidinyl]oxy]methanesulfonic acid, dipotassium salt

[3S-[3α(Z),4β]]-[[3-[[(2-Amino-4-thiazolyl)[(carboxymethoxy)imino]acetyl]amino]-4-[[(aminocarbonyl)oxy]methyl]-2-oxo-azetidinyl]oxy]methanesulfonic acid, dipotassium salt

[3S[3α(Z),4β]]-[[3-[[(2-Amino-4-thiazolyl)[[(1-carboxyl-1-methylethoxy)imino]acetyl]amino]-4-[[(aminocarbonyl)oxy]methyl]-2-oxo-1-azetidinyl]oxy]methanesulfonic acid, dipotassium salt

[3S-[3α(Z),4α]]-[[3-[[(2-Amino-4-thiazolyl)[(carboxymethoxy)imino]acetyl]amino]-4-[[(aminocarbonyl)oxy]methyl]-2-oxo-1-azetidinyl]oxy]methanesulfonic acid, dipotassium salt [3S(Z)]-[[3-[[(2-Amino-4-thiazolyl)[(1-carboxy-1-methylethoxy)imino]acetyl]amino]-4,4-dimethyl-2-oxo-1-azetidinyl]oxy]methanesulfonic acid, dipotassium salt

[3S(Z)]-[[3-[[(2-Amino-4-thiazolyl)[(carboxymethoxy)imino]acetyl]amino]-4,4-dimethyl-2-oxo-1-azetidinyl]oxy]methanesulfonic acid, dipotassium salt

[3S(Z)]-[[(3-[[(2-Amino-4-thiazolyl)(methoxyimino)acetyl]amino]-4,4-dimethyl-2-oxo-1-azetidinyl]oxy]methanesulfonic acid, monopotassium salt.

What is claimed is:
1. A β-lactam having the formula

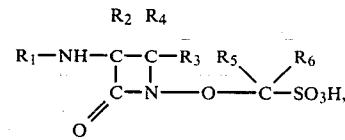

or a pharmaceutically acceptable salt thereof, wherein
$R_1$ is an acyl group derived from a carboxylic acid;
$R_2$ is hydrogen or methoxy;
$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, carboxyl, $—CH_2—X_1$, $—S—X_2$, $—O—X_2$,

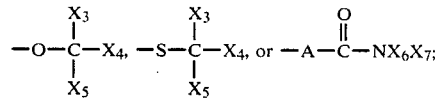

$R_5$ and $R_6$ are the same or different and each is hydrogen, alkyl, alkenyl, alkynyl, phenyl, subtituted phenyl, cycloalkyl or a 4, 5, 6 or 7-membered heterocycle, or $R_5$ and $R_6$ together with the carbon atom to which they are attached are cycloalkyl or a 4, 5, 6 or 7-membered heterocycle, or one of $R_5$ and $R_6$ is hydrogen and the other is azido, halomethyl, dihalomethyl, trihalomethyl, alkoxycarbonyl, 2-phenylethenyl, 2-phenylethynyl, carboxyl, $—CH_2—X_1$, $—S—X_2$, $—O—X_2$ or

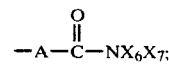

$X_1$ is azido, amino, hydroxy, alkanoylamino, alkylsulfonyloxy, phenylsulfonyloxy, (substituted phenyl)sulfonyloxy, phenyl, substituted phenyl, cyano, $—S—X_2$ or $—O—X_2$;

$X_2$ is alkyl, substituted alkyl, phenyl, substituted phenyl, phenylalkyl, (substituted phenyl)alkyl, alkanoyl, substituted alkanoyl, phenylcarbonyl, (substituted phenyl)carbonyl or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

A is —CH=CH—, —CH$_2$—CH=CH—, —(CH$_2$)$_n$—, —(CH$_2$)$_{n'}$—O—, —(CH$_2$)$_{n'}$—NH—, —(CH$_2$)$_{n'}$—S—CH$_2$—;

n is 0, 1, 2 or 3;

n' is 1 or 2; and

X$_6$ and X$_7$ are the same or different and each is hydrogen or alkyl, or X$_6$ is hydrogen and X$_7$ is amino, substituted amino, acylamino or alkoxy;

wherein the terms "alkyl" and "alkoxy" refer to groups having 1 to 10 carbon atoms;

the term "cycloalkyl" refers to cycloalkyl groups having 3, 4, 5, 6 or 7 carbon atoms;

the term "substituted alkyl" refers to alkyl groups substituted with one, or more, azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the terms "alkanoyl", "alkenyl" and "alkynyl" refer to groups having 2 to 10 carbon atoms;

the term "substituted alkanoyl" refers to a group having the formula (substituted alkyl)

or phenylalkanoyl;

the term "substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms) or carboxyl groups;

the term "substituted amino" refers to a group having the formula —NY$_1$Y$_2$ wherein Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylmethyleneamino, phenylmethyleneamino, substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl, hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylmethyleneamino, phenylmethyleneamino or substituted alkyl, wherein the alkyl group has 1 to 4 carbon atoms, groups.

2. A β-lactam in accordance with claim 1, a salt of [3S-[3α(Z),4α]]-[[3-[[(2-amino-4-thiazolyl)(methoxyimino)acetyl]amino]-4-methyl-2-oxo-1-azetidinyl]oxy]methanesulfonic acid.

3. A β-lactam in accordance with claim 1, a salt of [3S-[3α,(Z)4α]]-2-[[[1-(2-amino-4-thiazolyl)-2-[[4-methyl-2-oxo-1-(sulfomethoxy)-3-azetidinyl]-amino]-2-oxoethylidene]amino]oxy]-2-methylpropanoic acid.

4. A β-lactam in accordance with claim 1 wherein R$_2$ is hydrogen.

5. A β-lactam in accordance with claim 4 wherein R$_3$ and R$_4$ are each hydrogen.

6. A β-lactam in accordance with claim 4 wherein R$_3$ is hydrogen and R$_4$ is methyl.

7. A β-lactam in accordance with claim 4 wherein R$_3$ is methyl and R$_4$ is hydrogen.

8. A β-lactam in accordance with claim 4 wherein R$_5$ and R$_6$ are each hydrogen.

9. A β-lactam in accordance with claim 4 wherein R$_5$ and R$_6$ are each methyl.

10. A β-lactam in accordance with claim 4 wherein R$_1$ is (Z)-2-amino-α-[(1-carboxy-1-methylethoxy)imino]-4-thiazoleacetyl.

11. A β-lactam in accordance with claim 1 wherein R$_2$, R$_3$, R$_4$, R$_5$ and R$_6$ are each hydrogen.

12. A β-lactam in accordance with claim 1 wherein R$_2$, R$_3$, R$_5$ and R$_6$ are each hydrogen and R$_4$ is methyl.

13. A β-lactam in accordance with claim 1 wherein R$_2$, R$_4$, R$_5$ and R$_6$ are each hydrogen and R$_3$ is methyl.

14. A β-lactam having the formula

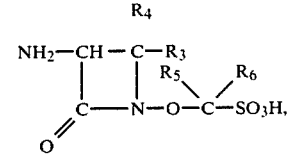

or a salt thereof, wherein

R$_3$ and R$_4$ are the same or different and each is hydrogen, alkyl, alkenyl, alkynyl, cycloalkyl, phenyl, substituted phenyl or a 4, 5, 6 or 7-membered heterocycle, or one of R$_3$ and R$_4$ is hydrogen and the other is azido, halomethyl, dihalomethyl, trihalomethyl, alkoxycarbonyl, 2-phenylethenyl, 2-phenylethynyl, carboxyl, —CH$_2$X$_1$, —S—X$_2$, —O—X$_2$,

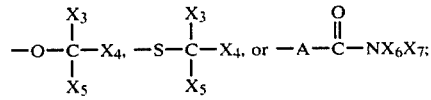

R$_5$ and R$_6$ are the same or different and each is hydrogen, alkyl, alkenyl, alkynyl, phenyl, subtituted phenyl, cycloalkyl or a 4, 5, 6 or 7-membered heterocycle, or R$_5$ and R$_6$ together with the carbon atom to which they are attached are cycloalkyl or a 4, 5, 6 or 7-membered heterocycle, or one of R$_5$ and R$_6$ is hydrogen and the other is azido, halomethyl, dihalomethyl, trihalomethyl, alkoxycarbonyl, 2-phenylethenyl, 2-phenylethynyl, carboxyl, —CH$_2$—X$_1$, —S—X$_2$, —O—X$_2$ or

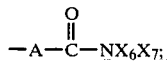

$X_1$ is azido, amino, hydroxy, alkanoylamino, alkylsulfonyloxy, phenylsulfonyloxy, (substituted phenyl)sulfonyloxy, phenyl, substituted phenyl, cyano, —S—$X_2$ or —O—$X_2$;

$X_2$ is alkyl, substituted alkyl, phenyl, substituted phenyl, phenylalkyl, (substituted phenyl)alkyl, alkanoyl, substituted alkanoyl, phenylcarbonyl, (substituted phenyl)carbonyl or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

A is —CH=CH—, —CH$_2$—CH=CH—, —(CH$_2$)$_n$—, —(CH$_2$)$_{n'}$—O—, —(CH$_2$)$_{n'}$—NH—, —(CH$_2$)$_{n'}$—S—CH$_2$—;

n is 0, 1, 2 or 3;

n' is 1 or 2; and $X_6$ and $X_7$ are the same or different and each is hydrogen or alkyl, or $X_6$ is hydrogen and $X_7$ is amino, substituted amino, acylamino or alkoxy;

wherein the terms "alkyl" and "alkoxy" refer to groups having 1 to 10 carbon atoms;

the term "cycloalkyl" refers to cycloalkyl groups having 3, 4, 5, 6 or 7 carbon atoms;

the term "substituted alkyl" refers to alkyl groups substituted with one, or more, azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the terms "alkanoyl", "alkenyl" and "alkynyl" refer to groups having 2 to 10 carbon atoms;

the term "substituted alkanoyl" refers to a group having the formula (substituted alkyl)

or phenylalkanoyl;

the term "substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms) or carboxyl groups;

the term "substituted amino" refers to a group having the formula —N$Y_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylmethyleneamino, phenylmethyleneamino substituted alkyl, wherein the alkyl group has 1 to 4 carbon atoms, groups;

the terms "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, teterazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl, hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylmethyleneamino, phenylmethyleneamino or substituted alkyl, wherein the alkyl group has 1 to 4 carbon atoms, groups.

15. A β-lactam in accordance with claim 1, a salt of [3S-[3α(Z),4β]]-2-[[[1-(2-amino-4-thiazolyl)-2-[[4-methyl-2-oxo-1-(sulfomethoxy)-3-azetidinyl]amino]-2-oxoethylidene]amino]oxy]-2-methylpropanoic acid.

16. A β-lactam in accordance with claim 14, [3S-(3α,4β)]-1-sulfomethoxy-3-amino-4-methyl-2-oxo-1-azetidine.

17. A β-lactam in accordance with claim 1, a salt of [3S-[3α(R), 4β]]-[[3-[[[[(4-ethyl-2,3-dioxo-1-peperazinyl)carbonyl]amino]phenylacetyl]amino]-4-methyl-2-oxo-1-azetidinyl]oxy]methanesulfonic acid.

18. A β-lactam in accordance with claim 1, a salt of [3S-[3α(Z),4β]]-[[3-[[(2-amino-4-thiazolyl)(methoxyimino)acetyl]amino]-4-methyl-2-oxo-1-azetidinyl]oxy]methanesulfonic acid.

19. A β-lactam in accordance with claim 14, [3S-(3α,4α)]-1-sulfomethoxy-3-amino-4-methyl-2-oxo-1-azetidine.

* * * * *